(12) United States Patent
Rowe

(10) Patent No.: US 12,138,389 B2
(45) Date of Patent: Nov. 12, 2024

(54) MANUAL RESUSCITATOR, VENTILATION CONTROL ASSEMBLY, AND METHOD OF USE

(71) Applicant: Jonathon D. Rowe, Valparaiso, IN (US)

(72) Inventor: Jonathon D. Rowe, Valparaiso, IN (US)

(*) Notice: Subject to any disclaimer, the term of this patent is extended or adjusted under 35 U.S.C. 154(b) by 918 days.

(21) Appl. No.: 17/197,448

(22) Filed: Mar. 10, 2021

(65) Prior Publication Data

US 2021/0283354 A1 Sep. 16, 2021

Related U.S. Application Data

(60) Provisional application No. 62/987,357, filed on Mar. 10, 2020.

(51) Int. Cl.
*A61M 16/00* (2006.01)

(52) U.S. Cl.
CPC .... *A61M 16/0072* (2013.01); *A61M 16/0084* (2014.02); *A61M 2205/3337* (2013.01); *A61M 2205/3379* (2013.01)

(58) Field of Classification Search
CPC .......... A61M 16/0072; A61M 16/0084; A61M 16/209; A61M 2205/3337; A61M 2205/3339

See application file for complete search history.

(56) References Cited

U.S. PATENT DOCUMENTS

| | | | |
|---|---|---|---|
| 3,973,564 A * | 8/1976 | Carden | A61M 16/0045 128/205.14 |
| 4,782,831 A | 11/1988 | Gallant | |
| 5,628,305 A * | 5/1997 | Melker | A61M 16/0075 128/205.15 |
| 8,443,804 B2 * | 5/2013 | Lee | A61M 16/0875 128/205.15 |
| 2014/0311486 A1 * | 10/2014 | Robitaille | A61M 16/209 128/204.19 |
| 2017/0157348 A1 * | 6/2017 | Gillespie | A61M 16/0816 |
| 2019/0060592 A1 | 2/2019 | Kuypers et al. | |

FOREIGN PATENT DOCUMENTS

| | | |
|---|---|---|
| CN | 204699191 | 10/2015 |
| CN | 205127046 | 4/2016 |

OTHER PUBLICATIONS

International Search Report & Written Opinion for PCT/US2021/021672, dated Jun. 30, 2021, (9 pages).

* cited by examiner

*Primary Examiner* — Valerie L Woodward
(74) *Attorney, Agent, or Firm* — Hartman Global IP Law; Gary M. Hartman; Domenica N. S. Hartman

(57) ABSTRACT

Manual resuscitators, ventilation control assemblies, and methods suitable for delivering a volume-controlled tidal volume of air to a patient's lungs. Such a resuscitator has a piston that pushes a selected volume of air out of a ventilation chamber of a cylinder in response to pressurized gases being introduced into an actuation chamber of the cylinder. A volume adjuster adjusts the maximum tidal volume of patient air that the piston pushes out of the ventilation chamber by adjusting the maximum length of the piston stroke in the cylinder. The volume adjuster may have a bypass mode that allows the manual resuscitator to operate without volume control. The manual adjuster may also be pressure regulated by one or more pressure regulation valves.

20 Claims, 5 Drawing Sheets

MANUAL RESUSCITATOR, VENTILATION CONTROL ASSEMBLY, AND METHOD OF USE

CROSS-REFERENCE TO RELATED APPLICATIONS

This application claims the benefit of provisional U.S. Patent Application No. 62/987,357, filed Mar. 10, 2020, the contents of which are incorporated by reference herein in their entirety.

BACKGROUND OF THE INVENTION

The present invention generally relates to equipment and methods for performing resuscitation. The invention particularly relates to manual resuscitators, ventilation control assemblies for manual resuscitators, and method of manually resuscitating a patient with a manual resuscitator.

When a person stops breathing spontaneously, it is known in the medical field to attempt to resuscitate the person through various methods of ventilating fresh air and/or oxygen into the person's lungs until such time as the person begins breathing spontaneously again. A manual resuscitator is a device specially adapted to ventilate a patient in this situation. A manual resuscitator is particularly useful in emergency, field, or mobile situations where larger ventilations devices, such as a computer and/or electronically controlled automated ventilator, are typically unavailable or otherwise cannot be easily accessed. In contrast to an automated ventilator, a manual resuscitator is typically of a size and form factor that can be easily transported, manipulated, and operated by hand by a single person on a patient.

A danger of artificially ventilating a patient is to over pressurize and/or over inflate the patient's lungs. For example, over inflation of the lungs can directly or indirectly lead to hypocarbia, intraventricular hemorrhaging, and/or other complications. In general, it is known that the lungs of a grown adult typically can safely receive a larger volume of air than the lungs of child, and the lungs of a child typically can safely receive a larger volume of air than the lungs of an infant. One method to protect against over-ventilation is to control the maximum air pressure delivered by a resuscitator to the lungs. Thus, a pressure-controlled resuscitator typically includes one or more pressure regulation valves, such as a pressure relief valve or pop-off valve, to prevent over pressurization of the gases forced into the patient's lungs.

FIGS. 3 through 5 show an exemplary arrangement of a pressure-controlled manual resuscitator 500 for reference. The manual resuscitator 500 includes a main body 508 that defines an internal air flow chamber. The main body 508 is generally in the form of an elbow so as to have a main stem extending longitudinally along an axis and two arms extending transversely to the axis in opposite directions from the main stem at a front end of the main body 508. A patient mask 505 is connected to a patient interface port 509 defined by one arm of the main body 508. A flow-inflating bag, or resuscitator bag 506, is connected to an actuation port 510 at a back end of the main stem of the main body 508. A manometer 501 with a dial indicator is connected to the other arm of the main body 508 and is fluidly coupled with the air flow chamber within the main body 508. The manometer 501 measures and displays the pressure inside the air flow chamber. A pop-off pressure limiting valve 502 is connected to the main stem of the main body 508 and is fluidly coupled with the air flow chamber. The pressure limiting valve 502 regulates the peak inspiration pressure (PIP) delivered by the resuscitator 500 by releasing gases from the air flow chamber when the gases exceed a set pressure. A first connection port 503 through the main stem of the main body 508 may be used to inject medicine into the air flow chamber. A second connection port 504 through the main stem of the main body 508 may be used to provide a patient air supply. A PEEP (Positive End Expiratory Pressure) valve 507 with an adjustment interface is connected to the main stem of the main body 508 and fluidly coupled with the air flow chamber within the main body 508. In operative use, the face mask 505 is fitted over and around the mouth and nose of a patient, and then the patient is ventilated by manually squeezing the resuscitator bag 506. The pressure limiting valve 502 prevents over pressurization of the patient's lungs by releasing air from the air flow chamber if the gases inside exceed the set pressure of the pressure limiting valve 502. When the operator stops squeezing the air bladder, the patient exhales automatically, the PEEP valve 507 and/or the pressure limiting valve 502 allow the exhaled air to escape from the air flow chamber, and the air bladder resumes its original shape. The process can then be repeated.

FIGS. 6 through 8 show a T-piece 550 for reference that can be used with various types of resuscitators including manual resuscitators. The T-piece 550 includes a main body 551 that defines an air flow chamber. The main body 551 is generally in the form of a T-piece so as to have a main stem extending longitudinally along an axis and two arms extending transversely to the axis in opposite directions from the main stem at a front end of the main stem of the main body 551. A PEEP valve assembly 552 is connected to a port defined at an end of one of the arms of the main body 551. The face mask 505 is coupled to a patient interface port defined at the end of the other arm of the main body 551. A connection port 555 is formed at the back end of the main stem of the main body 551. Flexible tubing 556 is connected to the connection port 555 and to a pressure regulated air supply 557, such as a pressure regulated air supply that could be produced by the manual resuscitator 500 of FIGS. 3 through 5, another type of manual resuscitator, or an automatic resuscitator. The PEEP valve assembly 552 includes a valve body, a screw adjustment, and a cap. The PEEP valve assembly 552 also includes a PEEP exhaust port 553 for pressure control and/or flow blocking by the operator. The PEEP valve assembly 552 also includes a PEEP valve needle 554 for controlling flow of gases through the PEEP valve assembly 552.

Pressure-only regulated resuscitators can sometimes have undesirable limitations when used on smaller patients, such as infants, because the patient's lungs are more compliant relative to a given pressure than are the lungs of more mature patients. When using a pressure-only regulated resuscitator, particular concern with neonatal patients is that the neonate's lungs can sometimes be over inflated and become hypocarbic. Also, with intubation and administration of surfactants, rapid changes in lung compliance relative to a given set pressure can occur, leading to possible over inflation of the lungs. Such risks may be addressed by controlling the maximum volume of gases that are forced into a patient's lungs in a single ventilation cycle, known as the tidal volume, using a volume-controlled resuscitator. Such a resuscitator typically includes a mechanism that controls the tidal volume that is delivered in a given artificial ventilation cycle. Typically, a larger patient, such as an adult, will have a larger safe tidal volume capacity and a smaller patient, such as an infant, will have a smaller safe tidal volume capacity. Various formulas are known to medical personnel that correlate the weight or other size parameters of a patient with an assumed safe tidal volume.

U.S. Pat. No. 4,782,831 discloses a volume-controlled manual resuscitator that allows the operator to preselect a maximum tidal volume gas that is ventilated into a patient's lungs. An inflatable air bladder is disposed inside a perforated cylinder inside a main pressure chamber. The air bladder is fluidly coupled with squeezable bulb on the exterior of the main pressure chamber. Inflating the air bladder by squeezing the bulb displaces air inside the main pressure chamber out through a conduit and eventually to the patient's lungs. A platform inside the perforated cylinder can be selectively moved axially along the perforated cylinder to be positioned closer or further from the air bladder with a threaded rod. Changing the position of the platform within the perforated cylinder selectively adjusts the maximum volume to which the air bladder can be inflated by the bulb, thereby selectively increasing or decreasing the tidal volume of gas that can be forced into the patient's lungs by the expansion of the air bladder during a ventilation cycle. Thus, the operator can select a preferred maximum tidal gas volume by advancing or retracting the platform with the threaded rod.

Use of an inflatable air bladder located inside the main pressure chamber may have some disadvantages. Therefore, it would be advantageous to have a manual resuscitator that allows an operator to control a maximum tidal volume without the use of an inflatable air bladder inside the main pressure chamber.

BRIEF SUMMARY OF THE INVENTION

The present invention provides manual resuscitators, ventilation control assemblies, and methods suitable for delivering a volume-controlled tidal volume of air to a patient's lungs. The manual resuscitators, ventilation control assemblies, and methods may be used for resuscitating human patients, though it is foreseeable that the manual resuscitators, ventilation control assemblies, and methods could be used on non-human patients that breath air with lungs, such as other mammals.

According to some aspects of the disclosure, a manual resuscitator is provided. In one arrangement, the manual resuscitator includes a piston disposed in a cylinder and a volume adjuster coupled to the cylinder and configured to adjust a maximum displacement volume of the piston in the cylinder. The cylinder extends along an axis from a rear end of the cylinder to a front end of the cylinder. The piston divides the cylinder into an actuation chamber at the rear end of the cylinder and a ventilation chamber at the front end of the cylinder. The ventilation chamber may be in fluid communication with a patient interface, and the actuation chamber may be in fluid communication with a resuscitator bag, such that actuating the resuscitator bag causes the piston to travel toward the front end of the cylinder and force gases out of the ventilation chamber to the patient interface up to the maximum displacement volume.

According to other aspects of the disclosure, a ventilation control assembly for a manual resuscitator is provided. In one arrangement, the ventilation control assembly includes a cylinder, a piston, and a volume adjuster. The cylinder extends along an axis from a rear end of the cylinder to a front end of the cylinder. The piston is disposed in the cylinder and divides the cylinder into an actuation chamber at the rear end of the cylinder and a ventilation chamber at the front end of the cylinder. The actuation chamber is configured to be in fluid communication with a resuscitator bag. The ventilation chamber may be in fluid communication with a patient interface port configured for connection with a patient interface to direct gas into the lungs of a patient. The volume adjuster is coupled to the cylinder and configured to adjust a maximum displacement volume of the piston in the cylinder. Pressurized gas introduced into the actuation chamber causes the piston to travel toward the front end of the cylinder and force gas out of the ventilation chamber toward the patient interface port.

According to other aspects of the disclosure, a method is provided for manually resuscitating a patient with a manual resuscitator as described above. A maximum displacement volume of the piston may be adjusted with a volume adjuster to a selected tidal volume of gas. The tidal volume of gas is preferably selected to be directly related to a size of the patient. A patient interface may be operatively coupled with the patient. The resuscitator bag may be actuated to ventilate the selected tidal volume of gas into the patient's lungs.

These and other aspects, arrangements, features, and/or technical effects will become apparent upon detailed inspection of the figures and the following description.

DETAILED DESCRIPTION OF THE INVENTION

Figure 1:
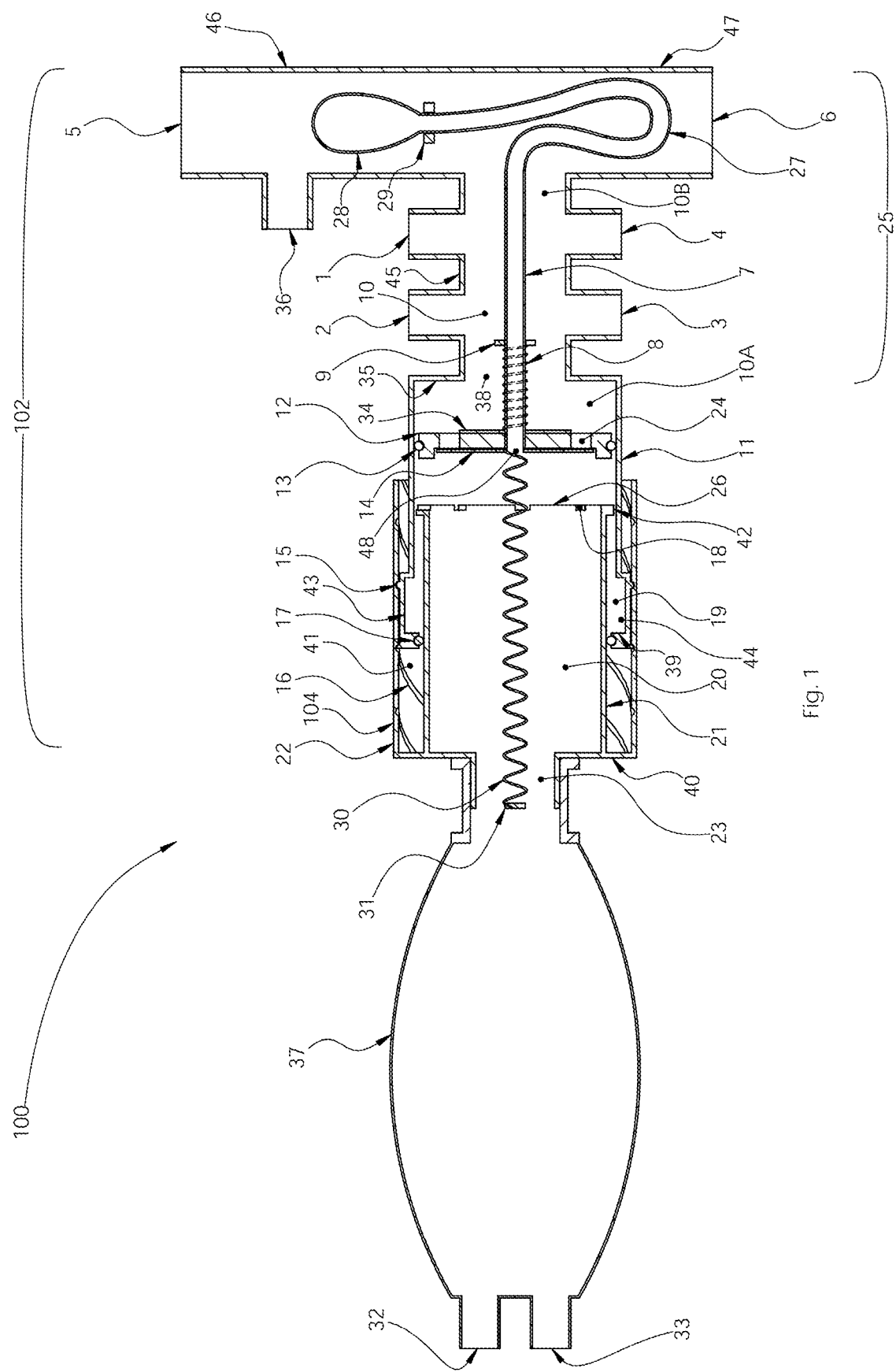
FIG. 1 is a side view of a longitudinal cross-section along a primary axis of a manual resuscitator according to a nonlimiting embodiment of the invention.

The intended purpose of the following detailed description and the phraseology and terminology employed therein is to describe what is shown in the drawings, which include certain nonlimiting embodiments of the invention, describe certain but not all aspects of the disclosed embodiments, and identify certain but not all alternatives of the disclosed embodiments. Therefore, the appended claims, and not the detailed description, serve to limit the scope of the invention.

Figure 2:
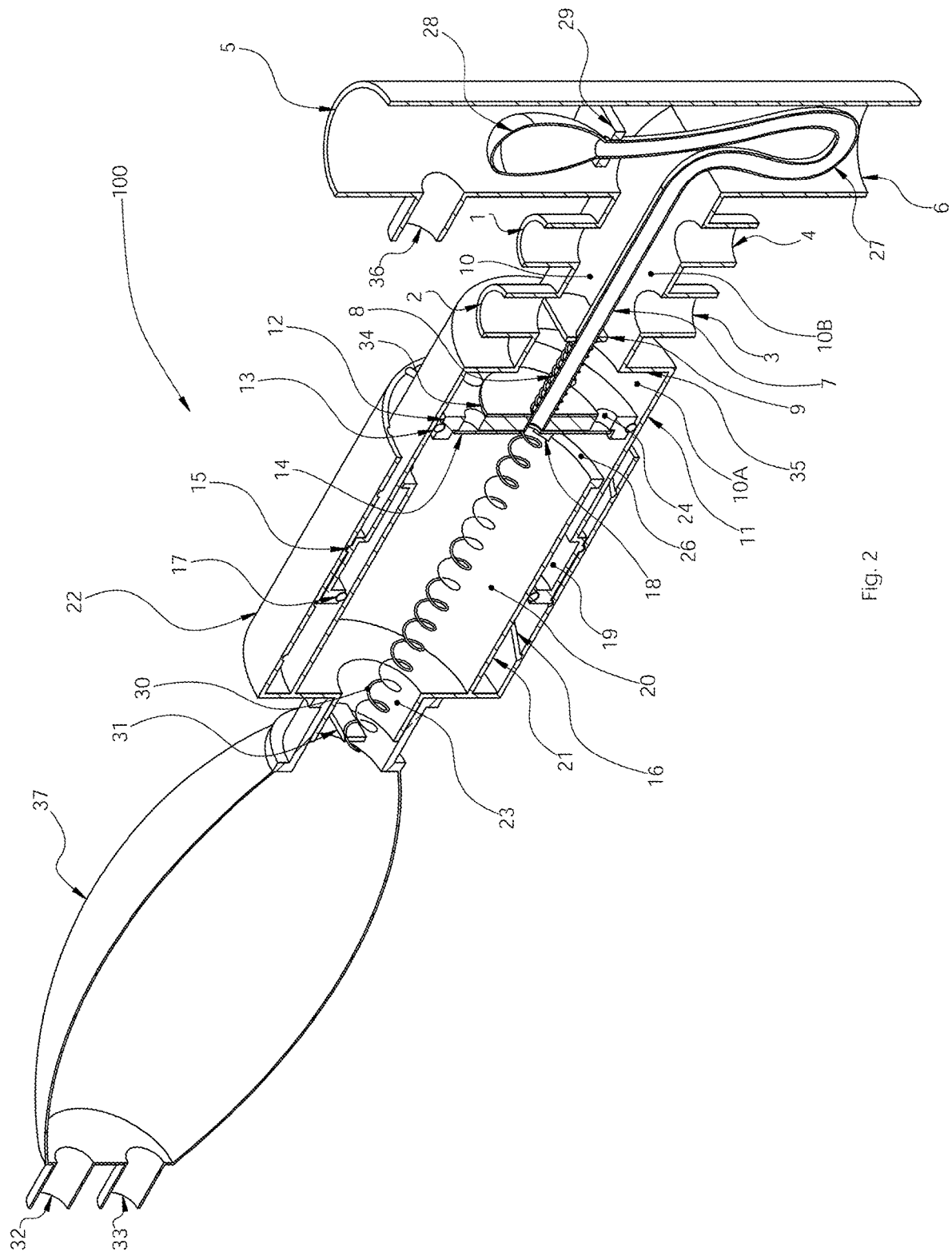
FIG. 2 is an orthographic view of the axial cross-section of the manual resuscitator of FIG. 1.
Figure 3:
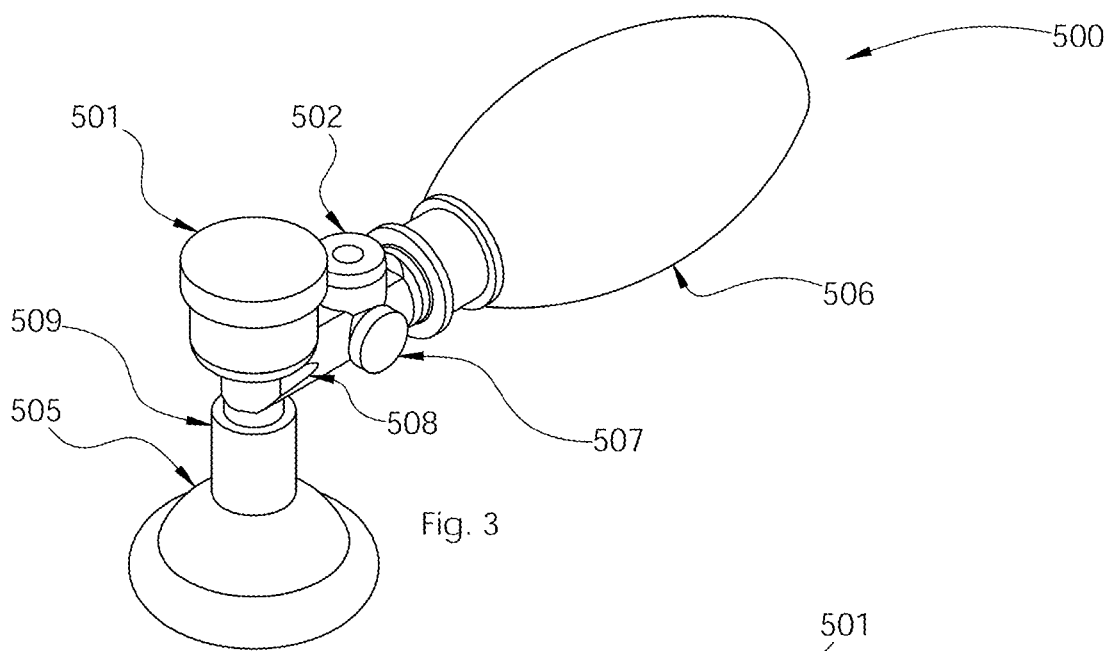
FIG. 3 is an orthographic view of a manual resuscitator according to the prior art.
Figure 4:
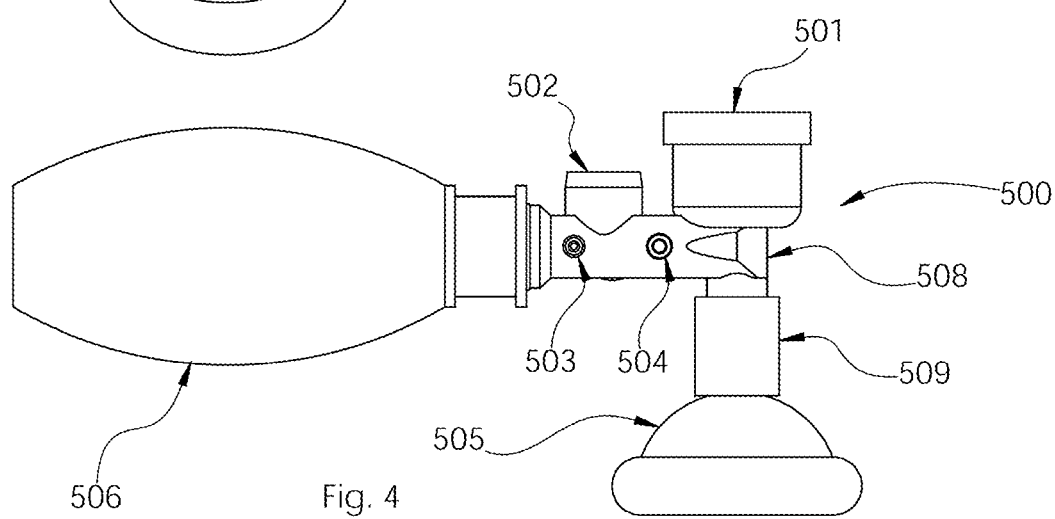
FIG. 4 is a side elevational view of the manual resuscitator of FIG. 3.
Figure 5:
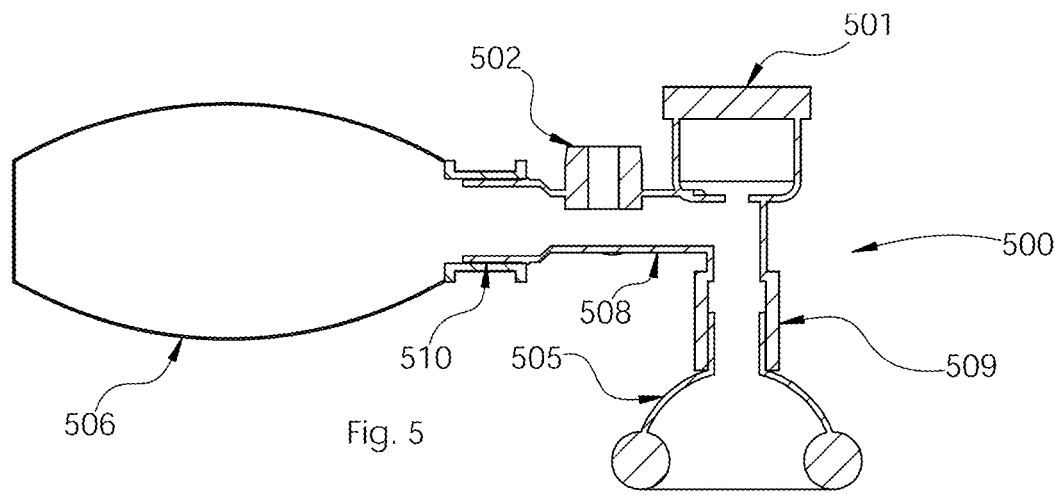
FIG. 5 is a side view of a longitudinal cross-section along a primary axis of the manual resuscitator of FIG. 3.
Figure 6:
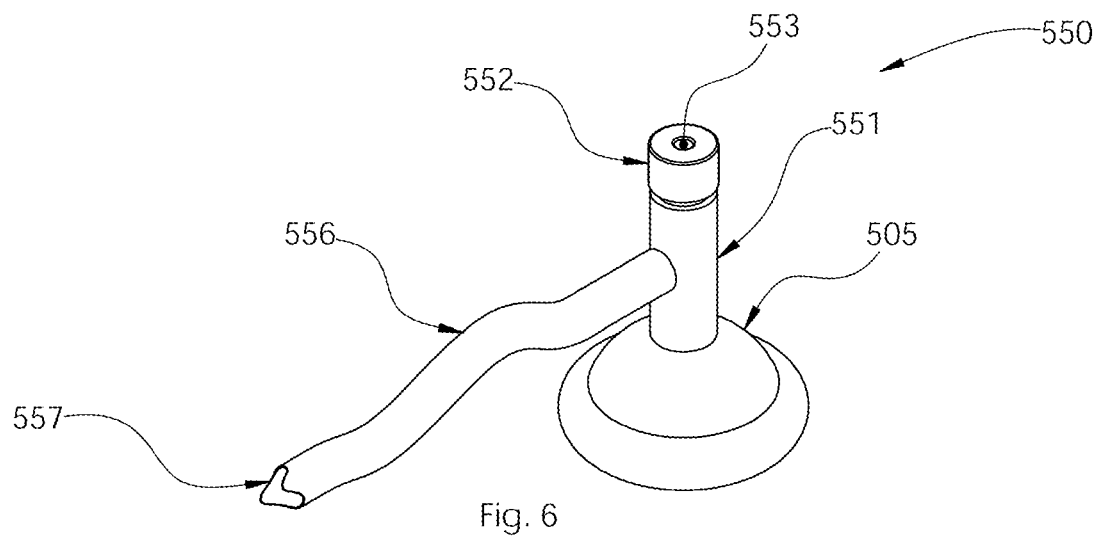
FIG. 6 is an orthographic view of a typical T-piece and face mask according to the prior art.
Figure 7:
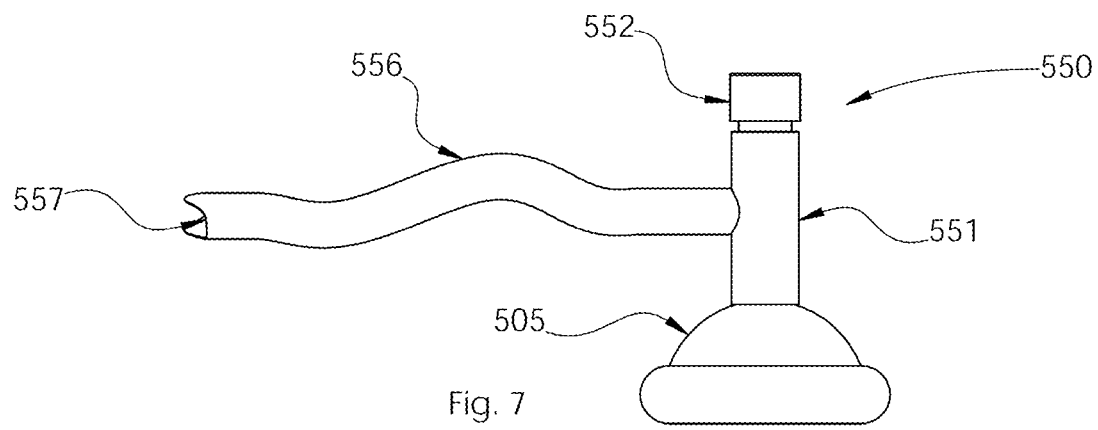
FIG. 7 is a side view of the T-piece of FIG. 6.
Figure 8:
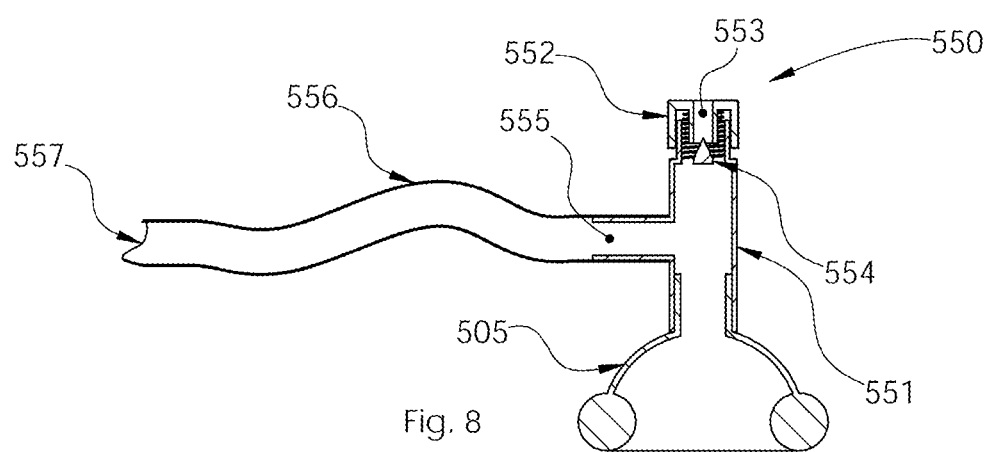
FIG. 8 is a side view of a longitudinal cross-section along a primary axis of the T-piece of FIG. 6.
Figure 9:
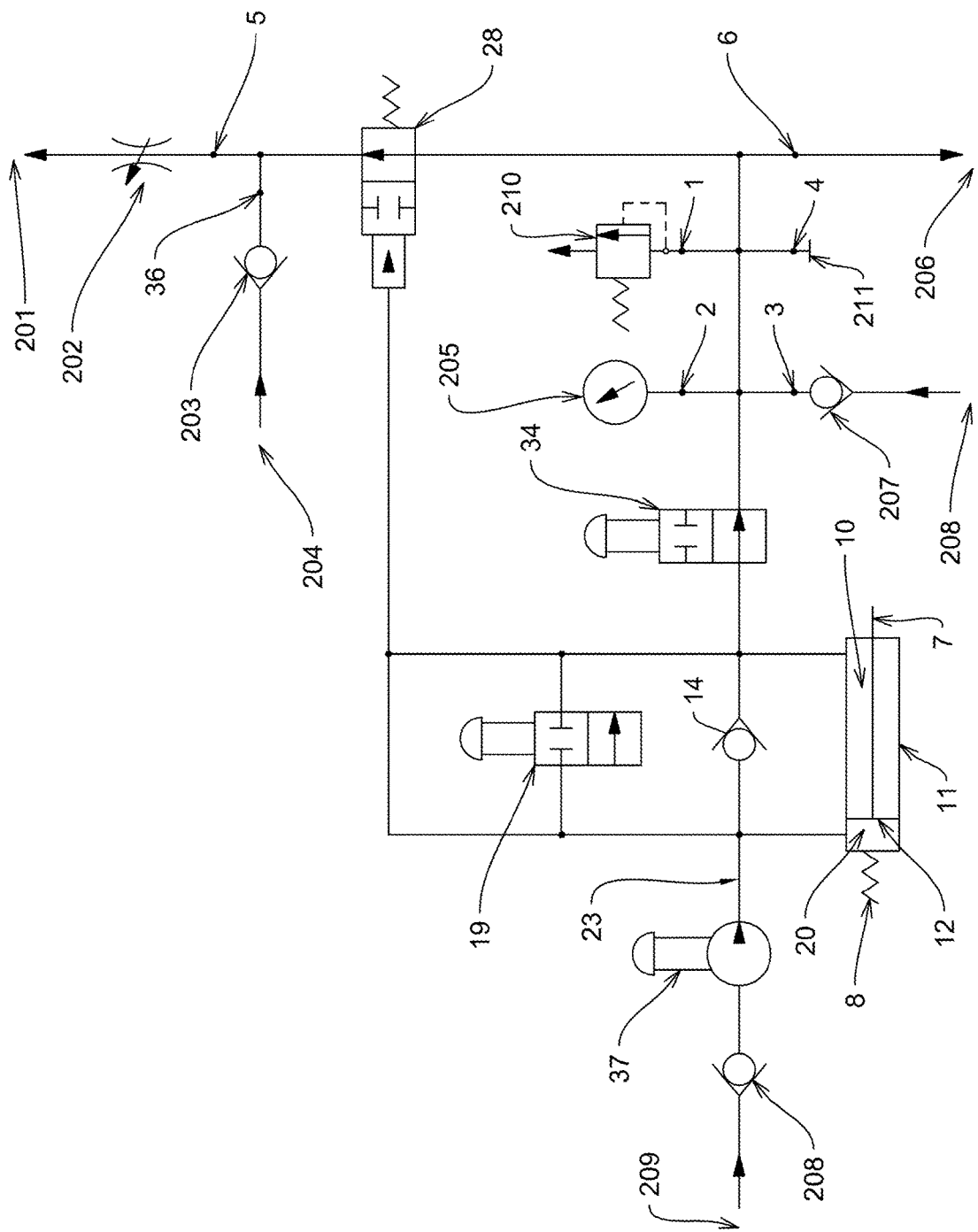
FIG. 9 is a pneumatic diagram of an exemplary operational arrangement of the manual resuscitator of FIG. 1.

Turning now to the exemplary arrangements of the drawings, FIGS. 1, 2, and 9 show portions of a manual resuscitator 100 according to certain exemplary aspects of the disclosure. The manual resuscitator 100 includes a resuscitator bag 37, a ventilation control assembly 102, and a patient connection interface. The patient connection interface may be any suitable device for engaging the patent and directing patent gases from the manual resuscitator into the patient's lungs. In the depicted arrangements, the patient connection interface is a patient face mask 505 (FIGS. 3 through 8); however, other patient connection interfaces, such as an endotracheal intubation tube, may also be used with the manual resuscitator 100. The resuscitator bag 37 is fluidly coupled with the ventilation control assembly 102 at a connector port 23 such that gases can be fluidly communicated therebetween. The patient connection interface is fluidly coupled with a front end of the ventilation control assembly 102 such that gases can be fluidly communicated therebetween. In operation, activating the resuscitator bag 37, such as by manually squeezing the resuscitator bag 37 by hand, forces a limited volume of gases out of the resuscitator bag 37 and into the ventilation control assembly 102, which subsequently forces a flow 206 of patient gases, such as air, oxygen, and/or other gas mixtures, from the front end of the ventilation control assembly 102, such as through the patient connection interface and into the patient's lungs, thereby ventilating the patient.

The ventilation control assembly 102 is configured to control the tidal volume of gas that is ventilated into the patient's lungs. The ventilation control assembly 102 includes a cylinder 11 extending from a front end to a rear end, a piston 12 disposed in the cylinder 11 that divides the internal volume of the cylinder 11 into a ventilation chamber 10A at the front end of the cylinder 11, and an actuation chamber 20 and volume adjuster 104 located at the rear end of the cylinder 11. The volume adjuster 104 shifts axially along the length of the cylinder 11 to extend axially into and retract axially out from the cylinder, which allows the effective length of the cylinder 11, i.e., the maximum stroke length of the piston 12 in the cylinder 11, to be selectively lengthened or shortened. By changing the effective length of the cylinder 11, the effective maximum displacement volume, or maximum tidal volume, of the ventilation chamber 10A inside the cylinder 11 is selectively enlarged or reduced. In this way, the maximum tidal volume of air that can be urged into the patient's lungs can be precisely controlled by extending or retracting the volume adjuster 104 relative to the cylinder 11. In this exemplary arrangement, the ventilation control assembly 102 also may be provided with one or more pressure regulating valves to control the maximum pressure of gases ventilated into the patient's lungs as depicted in FIG. 9 in addition to and/or as an alternative operation mode. However, addition of pressure regulation control is optional and may be omitted or not used in some operational arrangements and/or operation modes.

A manifold 25 is operatively coupled with the cylinder 11 and provides various ports and air chambers for coupling to various control components, interface components, and supplies. The manifold 25 defines a static volume chamber 10B fluidly coupled with the ventilation chamber 10A, which in combination define what may be referred to as an applied patient pressure chamber 10. The static volume chamber 10B is a chamber of static volume that forms an air flow path for patient supply gases that are to be ventilated into the patient's lungs. The manifold 25 in this example is connected with and extends from the front end of the cylinder 11. In other arrangements, the manifold 25 is separate from the cylinder 11, and for example, may be detachably connected to the cylinder 11 with a threaded connection, snap-lock connection, and/or one or more other suitable releasable connectors, and or be fluidly coupled with the cylinder 11 by a tube or hose that provides fluid communication between the ventilation chamber 10A and the static volume chamber 10B. Additional details of the manifold 25 are described in further detail hereinafter.

The cylinder 11 has a front end that connects to the manifold 25 and a rear end opposite the front end. A cylinder end wall 35 is disposed at the front end of the cylinder 11 and extends radially inwardly from the inner surface of the cylinder 11. An aperture 38 through the end wall 11 fluidly couples the ventilation chamber 10A with the static volume chamber 10B. A bypass area 19 is spaced axially apart from the front end of the cylinder 11, and preferably disposed near the rear end of the cylinder 11. The bypass area 19 includes one or more bypass air channel that allow air to bypass the piston 12 when located in the bypass area, as discussed in further detail hereinafter. A retention stop is formed by an inner annular lip 39 at the rear end of the cylinder 11 to prevent the volume adjuster 104 from sliding off of the rear end of the cylinder 11. The inner annular lip 39 extends radially inwardly from the inner surface of the cylinder 11 near ear the rear end of the cylinder. The cylinder 11 may be transparent or have see-through sections to allow the user to see into the interior of the cylinder. The cylinder 11 may be made of transparent plastic. Graduation lines (not shown) may be disposed on the cylinder 11 to help guide the user to set and observe the selected tidal volume of the cylinder.

The volume adjuster 104 has a rear end wall 40, a volume adjustment rod 21 extending forwardly from the rear end wall 40, and an adjuster body 22 extending forwardly from the rear end wall 40 and spaced radially outwardly from the volume adjustment rod 21. A radial gap 41 is defined between the outer surface of the volume adjustment rod 21 and the inner surface of the adjuster body 22. The radial gap 41 extends around the outer circumference of the volume adjustment rod 21 and extends from the front end of the volume adjustment rod to the rear end wall 104. The volume adjustment rod 21 has the form of a hollow tube, such as an inner cylindrical wall, extending from the rear end wall 40. The volume adjustment rod 21 at least partly defines the actuation chamber 20 and fluidly couples the connector port 23 with the rear face of the piston 12. The open rear end of the cylinder 11 slides into the radial gap 41 between the volume adjustment rod 21 and the adjuster body 22, the volume adjustment rod 21 slides into the rear end of the cylinder 11, and the adjuster body surrounds the cylinder 11. In this arrangement, the rearward portion of the cylinder 11 behind the piston 12 and the interior of the volume adjustment rod 21 together define the actuation chamber 20. The cylinder 11 slides axially along its longitudinal axis within the radial gap 41 between the volume adjustment rod 21 and the adjuster body 22 between a fully extended position and a fully retracted position. An outer annular lip 42 extends around the outer circumferential surface of the volume adjustment rod 21 near the front end. The outer annular lip 42 engages against the inner annular lip 39 of the cylinder 11 in the fully extended position to prevent the cylinder 11 from disengaging from the adjuster 104. The front end of the volume adjustment rod 21 forms a piston stop surface 26, or volume adjustment stop, that limits the travel stroke of the piston 12 in the cylinder 11 in the rearward direction, i.e., from the front end of the cylinder toward the rear end of the cylinder. The connector port 23 is disposed through the adjuster rear end wall 40 and provides a connection for operatively attaching the resuscitator bag 37 to the rear end of the adjuster 104. The connector port 23 may include any suitable airtight connection mechanism for fluidly coupling the resuscitator bag 37, or some other source of pressurized fluid, to the adjuster 104. In this arrangement, the connector port 23 is a cylindrical stub wall that can attach to a complementary connector on the resuscitator bag 37 and/or to another pressurized air source.

A volume rod adjustment seal, or adjuster seal 17, is disposed on the inner radial surface of the inner annular lip 39. The adjuster seal 17 forms a shiftable, airtight seal between the inner annular lip 39 and the outer surface of the volume adjustment rod 21 along the length of the inner cylindrical wall. The adjuster seal 17 may be any seal that can form an air-tight seal between the volume adjustment rod 21 and the inner surface of the cylinder 11 to maintain air pressure within the actuation chamber 20. Some exemplary seals include O-rings, X-rings, cup seals, and piston rings, and/or other seal types may be used.

FIGS. 1 and 2 show an exemplary adjusting mechanism for axially advancing and retracting the volume adjuster 104 on the cylinder 11. In this arrangement, the adjusting mechanism is a threaded, or screw-type mechanism. The cylinder 11 threadedly engages the volume adjuster 104 so that so that twisting the volume adjuster 104 relative to the cylinder 11 about the longitudinal axis of the cylinder 11 will advance or retract the adjuster 104 axially relative to the cylinder 11, depending on the direction of twisting. A helical guide 16 is disposed on the inner surface of the adjuster body 22 and engages with one or more guide followers 15, such as projections or helical ribs, on the outer surface of the outer surface of the cylinder 11 to provide a threaded engagement between the volume adjuster 104 and the cylinder 11. The guide followers 15 are disposed on a circumferential ridge 43 around the outer surface of the cylinder 11. The guide follower 15 and helical guide 16 may have any form suitable to provide the threaded engagement. In this arrangement, the helical guide 16 includes two parallel helical grooves, and the guide follower 15 includes two helical ribs that fit into the two helical grooves. However, other suitable threaded engagement mechanisms may be used. The outer surface of the adjuster body 22 forms a grip surface for an operator to easily grasp, manipulate, and twist the volume adjuster 104 with a single hand. Other mechanisms for linearly advancing and retracting the adjuster 104 from the cylinder 11 may be used. In another example, the threaded connection may be replaced with axially aligned linear tongue and groove interfaces. For example, axially aligned grooves on the inner surface of the adjuster body 22 may guide axial ribs on the outer surface of the volume adjustment rod 21. Detent notches may maintain the cylinder 11 in any one of a finite number of settings, or simple friction other detent mechanisms may be used to maintain the cylinder 11 in a selected position and allow infinite adjustability. Once a tidal volume setting is selected, the selected setting may be maintained by friction between the adjuster body 22 and the cylinder body 11 directly and/or through the adjuster seal 17 and/or with detent notches located within a groove of the helical guide 16 that engage with corresponding notches on a guide follower 15 at various positions to set pre-determined volumes.

The piston 12 slides axially forwards and rearward within the cylinder 11 and forms an airtight seal against the inner surface of the cylinder 11. A piston seal 13 is disposed around the outer circumferential sidewall of the piston to form the airtight seal with the inner surface of the cylinder 11, thereby fluidly separating the actuation chamber 20 and ventilation chamber 10A. The piston seal 13 may be any seal sufficient to create an air-tight seal between the piston 12 and the inner surface of the cylinder wall 11, such as an O-ring, X-ring, cup seal, or piston ring. A piston guide rod 7 extends from the front face of the piston 12 through the ventilation chamber 10A and through an alignment socket 9 that supports the forward end of the guide rod. The alignment socket 9 is located forward of the cylinder end wall 35 in the manifold 25 so as to not interfere with the stroke of the piston 12 between the cylinder end wall 35 and the piston stop surface 26. The piston guide rod 7 and alignment socket 9 are axially aligned with the stroke path of the piston 12 in the cylinder to guide the piston 12 along its stroke path. The piston guide rod 7 keeps the piston's face oriented perpendicular to the cylinder wall 11 and maintains motion of the piston 12 parallel to the longitudinal axis of the cylinder 11 to maintain a proper seal. In other arrangements, use of a self-guiding piston 12 may obviate the use of the piston guide rod 7.

The piston 12 is biased toward the rear of the cylinder 11 by a spring mechanism. The spring mechanism comprises one or more piston return springs, which in the nonlimiting embodiment of FIGS. 1 and 2 are represented as including a piston return compression spring 8 and a piston return extension spring 30. The piston return compression spring 8 is disposed on the front side of the piston 12 and pushes the piston 12 toward the rear of the cylinder 11. The piston return compression spring 8 may be a coil spring, a steel spring, a polywave spring, a conical spring, compressible foam, or any other resilient member suitable for pushing the piston 12 toward the rear of the cylinder 11. The piston return compression spring 8 is coiled around the piston guide rod 7 and extends from the alignment socket 9 to the front face of the piston 12. Thus, the piston guide rod 7 keeps the piston return compression spring 8 centered and assures its linear compression. The piston return compression spring 8 has a length sufficient to urge the piston 12 rearward in the cylinder 11 until the rear face of the piston 12 engages against the piston stop surface 26 at the front end of the volume adjustment rod 21. The piston return extension spring 30 is disposed on the on the rear side of the piston 12 and urges the piston 12 toward the rear of the cylinder 11. The piston return extension spring 30 is attached to a spring mount 31 in the adjuster 104 and to the back face of the piston 12. The piston return extension spring 30 pulls the piston 12 rearward toward the piston stop surface 26. The piston return extension spring 30 may be any resilient member suitable to pull the piston 12 toward the rear of the cylinder 11, such as a coil spring.

One or more piston check valves 14 are disposed through the piston 12 that allow gases to move through the piston 12 from the ventilation chamber 10A into the actuation chamber 20 and prevent movement of the gases from the actuation chamber 20 into the ventilation chamber 10A. The piston check valves 14 may be any one-way check valve suitable for controlling the flow of gases through the piston 12 as described herein. In the present arrangement, each piston check valve 14 includes a valve port 24, such as an aperture, through the piston from the front face to the rear face and a flap valve disposed on the rear face of the piston 12 and covering the valve port 24. Two or more piston check valves 14 are disposed through the piston 12; however, any number of piston check valves 14 may be used. Other, more complex mechanical check valve arrangements may be used. The piston check valves 14 are disposed radially inward of the piston stop surface 26 of the volume adjustment rod 21. In this position, the volume adjustment rod 21 and the piston stop surface 26 do not interfere with the functioning of the piston check valves 14. The piston check valves 14 are also disposed radially outwardly of the aperture 38 through the cylinder end wall 35. A radially central portion of the front face of the piston 12 forms a plug seal 34 that engages the cylinder end wall 35 when the volume adjuster 104 is fully advanced into the cylinder 11. The plug seal 34 provides an airtight seal for the static volume chamber 10B when the piston 12 is fully advanced and held against the cylinder end wall 35 in a zero-displacement mode. In this mode, the plug seal 34 prevents flow of air from the static volume chamber 10B either directly into the ventilation chamber 10A or into the actuation chamber 20 through the check valves 14, thereby minimizing dead space.

The volume adjuster 104 is operated by twisting the volume adjuster 104 relative to the cylinder 11 to either advance or retract the volume adjuster relative to the cylinder 11. The volume adjuster 104 can be adjusted between a bypass mode, in which the cylinder 11 is fully retracted from the adjuster body 22 and disposed in the bypass area, and a zero-displacement mode, or T-piece mode, in which the cylinder 11 is fully extended against the cylinder end wall 35 and provides zero effective volume of the ventilation chamber 10A. A volume control mode is defined in the space between the between fully retracted setting in bypass mode and the fully extended setting in the zero-displacement mode.

The bypass mode is active when the volume adjustment rod 21 is fully retracted, thereby allowing the piston return compression spring 8 and/or the piston return extension spring 30 to bias the piston 12 into the bypass area 19 of the cylinder. The bypass mode is selected by twisting the volume adjuster 104 in a first direction on the cylinder 11 until the volume adjuster is in the fully retracted position. In the bypass mode, air in the actuation chamber 20 can bypass the piston by following a bypass path around the outer edge of the piston 12 defined by the one or more bypass channels in the cylinder wall. The bypass channels have a length able to traverse the width of the piston 12 when the piston is in the bypass area 19 to allow air to travel past the outer edge of the piston from the actuation chamber 20 to the ventilation chamber 10A. In the present exemplary arrangement, the bypass channel is defined by a circumferential groove 44 recessed into the inner surface of the cylinder 11. The circumferential groove 44 has an axial length that is longer than the width of the circumferential sidewall of the piston 12. In other arrangements, the bypass channel may be defined by one or more longitudinal channels in the cylinder wall or other types of air conduits. One or more bypass air channels 18 disposed in the piston stop surface 26 allow gases to flow from inside the volume adjustment rod 21 to the outer periphery of the piston 12 into the bypass air channel(s) when the back face of the piston 12 is pressed against the piston stop surface 26. Thus, when the volume adjustment rod is fully retracted (to the left in FIG. 1) and the piston 12 is held against the piston stop surface 26 by the springs 8 and/or 30, one air flow channels formed by the bypass air channels 18 and the circumferential groove 44 in the cylinder walls form an air bypass path that allows air to flow around the piston. In the bypass mode, the manual ventilator 100 operates generally similarly to existing commonly used resuscitators without tidal volume control. In this mode, compression of the resuscitator bag 37 by the operator will directly result in increased pressure in the ventilation chamber 10A and flow to the patient. Thus, in this mode, the manual resuscitator 100 can function like a typical pressure regulated manual resuscitator without controlling the volume of gases ventilated into the patient's lungs.

In the volume control mode, the maximum tidal volume of gases that can be ventilated into the patient's lungs is limited directly relative to the effective volume of the ventilation chamber 10A as controlled by lengthening or shortening the piston stroke with the axial position of the piston stop surface 26 inside the cylinder 11. The volume control mode is engaged by twisting the volume adjuster 104 on the cylinder 11 so that the piston stop surface 26 is disposed at any position between and spaced apart from the bypass area 19 and the cylinder end wall 35. A specific tidal volume can be selected by further adjusting the position of the piston stop surface 26, and thus the stroke length of the piston 12, to a selected position along the axis of the cylinder corresponding to a selected effective cylinder volume. By thus adjusting the effective length of the cylinder 11, the volume of gases forced from the ventilation chamber 10A into the static volume chamber 10B and from there into the patient's lungs can be limited to various selected maximum tidal amounts. Preferably, markings or other measurement references are provided to correlate the axial position of the piston stop surface 26 with the resultant maximum tidal volume to help the operator to quickly adjust the volume adjuster 104 to a desired tidal volume setting. In some size variants, the maximum tidal volume can be adjusted from about between 2000 ml to 0 ml. In size variants specifically designed for infant and neonatal use, the maximum tidal volume can be adjusted with extreme accuracy preferably from about 200 ml to 0 ml, more preferably from about 60 ml to 0 ml, even more preferably from about 40 ml to 2 ml. However, the specific size and volume ranges are exemplary only and other tidal volume ranges may be implemented. In operation, pressure is generated in the actuation chamber 20 by the operator's compression of the resuscitator bag 37. The increased pressure in the actuation chamber 20 moves the piston 12 forward against the force of the springs 8 and/or 30 and displaces the selected tidal volume out of the ventilation chamber 10A and through the patient port 6 in the manifold 25. Thus, use of the movable piston 12 obviates the use of an inflatable bladder inside the body of the ventilation control assembly 102.

In the zero-displacement mode, the volume adjuster 104 is fully extended into the cylinder 11 such that that piston stop surface 26 presses the plug seal 34 at the front face of the piston 12 directly against the cylinder end wall 35. In this position, the piston 12 has a stroke length of 0, and the ventilation chamber has an effective volume of 0. In this mode, the manual resuscitator 100 may be used generally like a common T-piece device when a common pressure regulated air source, such as a Neopuff or Radiant Warmer, is operatively coupled to the manifold 25. This mode minimizes dead space by sealing off the actuation chamber 20 from the ventilation chamber 10A.

Turning now to other parts of the manual resuscitator 100, the manifold 25 may take any form suitable for transferring gases from the ventilation chamber 10A to a patient interface device, such as the face mask 505. The body of the manifold exemplified in the drawings is in the generally in the form of a T, including a main body 45 that is hollow and extends along a first central axis, and pair of upper and lower hollow arms 46 and 47 extending in opposite directions from the main body 45 along a second axis generally perpendicular to the first central axis. The first central axis is coaxial with the central axis of the cylinder 11; however, the body of the static pressure chamber is not limited to this particular shape and arrangement. The manifold 25 has a rigid body with connection ports through the main body into the static volume chamber 10B that provide fluid connection into the static volume chamber 10B for connection to various devices and supplies. In this example, the ports provided include a valve port 1, a pressure sensor port 2, a gas supply port 3, a utility port 4, a PEEP connection port 5, a patient interface port 6, and a supply port 36. Ports 1-6 extend radially outwardly from the main body 45. The PEEP connection port 5 is disposed at the distal end of the upper arm 46. The patient interface port 6 is disposed at the distal end of the lower hollow arm 47. The supply port 36 extends off of the upper hollow arm 46 between the PEEP connection port 5 and the main body 45, thereby fluidly disposed between the static volume chamber 10B and the PEEP connection port 5.

A block valve 28 is disposed in the upper hollow arm 46 between the PEEP connection port 5, the supply port 36, and the main body 45. The block valve 28 is arranged to selectively block the PEEP connection port 5 and the supply port 36 from the main body 45 when the actuation chamber 20 is pressurized to ventilate the patient. The block valve 28 is a pilot-operated block valve including an inflatable balloon mounted in the upper hollow arm 46 with a valve mount 29 and a pilot tube 27 that fluidly connects the actuation chamber 20 to the interior of the inflatable balloon. The valve mount 29 provides a fixed location and mount for the block valve 28. The pilot tube 27 is a flexible tube that is connected to the piston guide rod 7. The piston guide rod 7 is a hollow tube that extends from a pilot orifice 48 through the piston 12 and at least partly defines a conduit that fluidly connects the actuation chamber 20 with the block valve 28. When the actuation chamber 20 is pressurized, for example by squeezing on the resuscitator bag 37, air travels through the conduit formed by the pilot orifice 48, the piston guide rod 7, and the pilot tube 27 into the balloon, thereby expanding the balloon to engage against the inner surface of the upper hollow arm 46 and sealing off the static volume chamber 10B from the PEEP device and the supply port 36. When pressure is released from the resuscitator bag 37, the balloon deflates, thereby returning gas flow between the PEEP connection port 5 and the supply port 36 and the static volume chamber 10B. Other types of block valves 28 may be used to block the PEEP connection port 5. For example, a non-pressure differential dependent valve (non-balloon style) valve may be used which directs the air pressure in the actuation chamber 20 against a spring return valve to close/block the PEEP connection port 5. The block valve 28 in either arrangement may be integral to the body of the static volume chamber 10B or may be separable from the body of the static pressure chamber.

The resuscitator bag 37 may have any form suitable for allowing an operator to selectively force air into the actuation chamber. For example, the resuscitator bag 37 may be a flexible air bladder that the operator can squeeze to eject air or other gases. The resuscitator bag 37 may include a self-inflating air bladder, a non-self-inflating air bladder, or any other mechanism configured to eject a limited volume of pressurized air or other gases upon actuation by an operation, such as a bellows, piston and cylinder arrangement, or other suitable arrangement. The resuscitator bag 37 may include one or more connection ports for connecting with various accessories. In this example, the resuscitator bag includes an air connection port 32 for connecting with a supply of pressurized air (not shown) and a valve port 33 for connecting to a check valve (not shown). Other types of resuscitator bags may be used.

FIG. 9 shows a pneumatic diagram of one possible functional arrangement of the manual resuscitator 100. For simplicity of illustration, FIG. 9 schematically represents certain but not all of the components of the resuscitator 100 described above in reference to FIGS. 1 and 2. The piston 12 is schematically represented in FIG. 9 along with its actuation chamber 20, applied patient pressure chamber 10 (comprising the unlabeled ventilation and static volume chambers 10A and 10B), and a single piston return spring (labeled as 8 in FIG. 9). Components schematically represented in FIG. 9 include a piston check valve 14 located in the piston 12 to prevent flow from the actuation chamber 20 to the ventilation chamber 10A, forcing increased pressure in the actuation chamber 20 to move the piston 12 forward while allowing air to replenish the volume in the actuation chamber 20 and the resuscitator bag 37 when the pressure in the ventilation chamber 10A is greater. Moving the volume adjuster 104 (not shown) to the rear of the cylinder 11 into the bypass area 19 (whose schematic equivalent is represented in FIG. 9) creates a flow path around the piston 12. Moving the volume adjuster 104 (not shown) to the front of the cylinder 11 creates the plug seal 34 (whose schematic equivalent is represented in FIG. 9).

FIG. 9 further represents a Positive End Expiratory Pressure (PEEP) valve 202, such as a commonly used PEEP valve shown in FIG. 8, operatively coupled to the PEEP valve port 5 to control pressure, particularly during an exhalation cycle. The PEEP valve 202 may be integral with the body of the static volume chamber 10B or connected as an accessory to the PEEP valve port 5. An air flow path 201 can pass from the static volume chamber 10B to the surrounding ambient environment through the block valve 28 and the PEEP valve 202. Supply port 36 is coupled with an air supply 204. The air supply may be a regulated supply of patient gas, such as a flow-regulated supply of air and/or oxygen, a pressure regulated supply of air and/or oxygen from a Neopuff, a supply of air from a radiant warmer, or the air supply may be ambient air when the manual ventilator 100 is used with a self-inflating bag. A check valve 203 is operatively coupled with the supply port 36 to prevent backflow into the air supply 204 during exhalation. A pressure measuring device 205, such as a manometer, is operatively coupled to the pressure sensor port 2 to sense the gas pressure inside the static volume chamber 10B. A patient air supply 208 is operatively connected to the gas supply port 3 to provide a supply of air (and/or other gases to be ventilated into the patient) into the static volume chamber 10B. The patient air supply is preferably a flow-regulated supply of air. A check valve 207 is operatively disposed along the patient air supply 208 to prevent backflow of air into the flow-regulated air supply 208. Patient ventilation air 206 flows through the patient interface port 6 from the static volume chamber 10B to a patient interface, such as the patient face mask 505. A first port plug 210 is operatively disposed to block air flow through the valve port 1. Alternatively, a pressure regulating valve may be coupled to the valve port 1, which regulates the maximum pressure that can be achieved within the static volume chamber 10B. The pressure regulating valve may be any valve suitable for use with the manual resuscitator that will release pressure at a predefined maximum pressure setting so to prevent the pressure within the static volume chamber 10B from exceeding the predefined maximum pressure setting, such as a pop-off valve. The pressure regulating valve may have a fixed pressure relief setting or may be adjustable to provide different pressure relief settings. A second port plug 211 is operatively disposed to block air flow through the valve port 2. The utility port 4 may be connected to one or more supplies 211 of other materials into the patient's lungs during ventilation, such as medicines, and/or to sensors, such as chemical and/or gas analysis devices, or other sensors. The resuscitator bag 37 is operatively coupled to the connector port 23 in the volume adjuster 104 to force air into the actuation chamber 20 of the cylinder 11. An actuation air supply 209 is operatively coupled to the resuscitator bag 37 to provide a supply of air to the resuscitator bag 37 and the actuation chamber 20. The actuation air supply 209 may be flow regulated or pressure regulated. The actuation air supply 209 may be ambient air when the resuscitator bag 37 is a self-inflating bag. A check valve 208 is operatively disposed along the supply route of the actuation air supply 209 to prevent backflow of air out from the resuscitator bag 37. This is just one nonlimiting exemplary arrangement in which the manual ventilator 100 and/or the ventilation control assembly 102 may be used. Other arrangements and combinations of air supplies, port plugs, valves, and other accessories and/or arrangements of accessories may be implemented by an operator in using the ventilation control assembly 102 and manual ventilator 100. The ports 1-6 and 36 are not limited to being connected to the specific equipment or source described, and the various pieces and types of equipment may be connected different ones of the ports. Any one or more of the connection ports 1-6 and 36 may be temporarily or permanently closed with a suitable plug if not to be used during a certain procedure, and/or may omitted altogether. Other arrangements for the manifold 25 and various connection ports may be used.

This detailed description and the drawings of the exemplary embodiments are to be construed as examples only and do not describe every possible embodiment or combination of features. One could implement numerous alternate embodiments, using either current technology or technology developed after the filing date of this application. Thus, while specific exemplary forms are illustrated and described herein, it is to be understood that any of the various aspects, arrangements, and/or features disclosed herein may be combined with any one or more of the other aspects, arrangements, and/or features disclosed herein in a manner that would be understood by a person of ordinary skill in view of the teachings of this disclosure. Therefore, the scope of the invention is to be limited only by the claims.

The invention claimed is:

1. A manual resuscitator comprising:
    a patient interface;
    a resuscitator bag;
    a piston disposed in a cylinder, the cylinder extending along an axis from a rear end of the cylinder to a front end of the cylinder, the piston dividing the cylinder into an actuation chamber at the rear end of the cylinder and a ventilation chamber at the front end of the cylinder, the actuation chamber in fluid communication with the resuscitator bag, and the ventilation chamber in fluid communication with the patient interface; and
    a volume adjuster coupled to the cylinder and configured to adjust a maximum displacement volume of the piston in the cylinder, the volume adjuster being adjustable between a bypass mode which allows gases from the actuation chamber to bypass the piston to enter the ventilation chamber and a volume control mode in which the piston prevents movement of gases from the actuation chamber into the ventilation chamber;
    wherein actuating the resuscitator bag causes the piston to travel toward the front end of the cylinder and force gases out of the ventilation chamber to the patient interface up to the maximum displacement volume.

2. The manual resuscitator of claim 1, wherein the volume control mode is between the bypass mode in which the cylinder is retracted into an adjuster body of the volume adjuster and a zero-displacement mode in which the cylinder is fully extended from the adjuster body and provides zero effective volume of the ventilation chamber.

3. The manual resuscitator of claim 1, wherein the cylinder includes a bypass channel, and wherein in the bypass mode, the bypass channel circumvents the piston and allows gases from the actuation chamber to enter the ventilation chamber.

4. The manual resuscitator of claim 3, wherein the bypass channel comprises a circumferential groove in an inner wall of the cylinder spaced axially apart from the front end of the cylinder.

5. The manual resuscitator of claim 1, further comprising a pressure regulating valve configured to limit a maximum pressure that can be developed in the ventilation chamber.

6. The manual resuscitator of claim 1, wherein the volume adjuster includes a piston stop surface that engages the piston and stops travel of the piston toward the rear end of the cylinder, and wherein the volume adjuster selectively shifts the piston stop surface axially forward and rearward along the cylinder.

7. The manual resuscitator of claim 6, further comprising a spring mechanism that biases the piston toward the piston stop surface.

8. The manual resuscitator of claim 7, wherein the spring mechanism includes at least one of a piston return spring that pushes against a front face of the piston and a piston extension spring that pulls against a rear face of the piston.

9. The manual resuscitator of claim 6, wherein the volume adjuster is threadedly engaged with the cylinder, wherein twisting the volume adjuster in a first direction advances the piston stop surface toward the front end of the cylinder and twisting the volume adjuster in a second direction retracts the piston stop surface toward the rear end of the cylinder.

10. The manual resuscitator of claim 1, further comprising a check valve carried by the piston, wherein the check valve allows gases to move through the piston from the ventilation chamber into the actuation chamber, and wherein the check valve prevents movement of gases through the piston from the actuation chamber into the ventilation chamber.

11. A method of manually resuscitating a patient with the manual resuscitator of claim 1, the method comprising:
    adjusting the maximum displacement volume of the piston with the volume adjuster to a selected tidal volume of gas directly related to a size of the patient;
    operatively coupling the patient interface with the patient; and
    actuating the resuscitator bag to ventilate the selected tidal volume of gas into the patient's lungs.

12. The method of claim 11, wherein the step of adjusting includes lengthening or shortening a maximum stroke length of the piston within the cylinder.

13. A manual resuscitator comprising:
    a patient interface;
    a resuscitator bag;
    a piston disposed in a cylinder, the cylinder extending along an axis from a rear end of the cylinder to a front end of the cylinder, the piston dividing the cylinder into an actuation chamber at the rear end of the cylinder and a ventilation chamber at the front end of the cylinder, the actuation chamber in fluid communication with the resuscitator bag, and the ventilation chamber in fluid communication with the patient interface; and
    a volume adjuster coupled to the cylinder and configured to adjust a maximum displacement volume of the piston in the cylinder;
    wherein actuating the resuscitator bag causes the piston to travel toward the front end of the cylinder and force gases out of the ventilation chamber to the patient interface up to the maximum displacement volume;
    wherein the volume adjuster includes a piston stop surface that engages the piston and stops travel of the piston toward the rear end of the cylinder, and wherein the volume adjuster selectively shifts the piston stop surface axially forward and rearward along the cylinder;

wherein the volume adjuster is threadedly engaged with the cylinder wherein twisting the volume adjuster in a first direction advances the piston stop surface toward the front end of the cylinder and twisting the volume adjuster in a second direction retracts the piston stop surface toward the rear end of the cylinder;

wherein the volume adjuster includes a volume adjustment rod extending into the rear end of the cylinder, wherein the volume adjustment rod defines at least a portion of the actuation chamber and an airflow path from the resuscitator bag to the actuation chamber, wherein the piston stop surface is located on the volume adjustment rod, and the manual resuscitator further comprises a bypass air channel in the volume adjustment rod, wherein the bypass air channel forms at least a portion of an air bypass path around the piston when the piston is engaged against the piston stop surface.

14. The manual resuscitator of claim 13, wherein the volume adjuster further includes
   a rear end wall; and
   an adjuster body extending from the rear end wall,
   wherein the volume adjustment rod extends from the rear end wall,
   wherein the adjuster body surrounds the volume adjustment rod,
   a radial gap is disposed between the adjuster body and the volume adjustment rod, and
   wherein the rear end of the cylinder is slidably disposed in the radial gap.

15. The manual resuscitator of claim 14, wherein the threaded engagement includes helical guide on an inner surface of the adjuster body that threadedly engages with a guide follower on the cylinder.

16. A manual resuscitator comprising:
   a patient interface;
   a resuscitator bag;
   a piston disposed in a cylinder, the cylinder extending along an axis from a rear end of the cylinder to a front end of the cylinder, the piston dividing the cylinder into an actuation chamber at the rear end of the cylinder and a ventilation chamber at the front end of the cylinder, the actuation chamber in fluid communication with the resuscitator bag, and the ventilation chamber in fluid communication with the patient interface;
   a volume adjuster coupled to the cylinder and configured to adjust a maximum displacement volume of the piston in the cylinder; and
   a piston guide rod connected with the piston and with a pilot-operated block valve, wherein the piston guide rod guides axial travel of the piston along the cylinder, and wherein the piston guide rod at least partly defines a conduit that fluidly connects the actuation chamber with the pilot-operated block valve;
   wherein actuating the resuscitator bag causes the piston to travel toward the front end of the cylinder and force gases out of the ventilation chamber to the patient interface up to the maximum displacement volume.

17. A ventilation control assembly for a manual resuscitator, the ventilation control assembly comprising:
   a cylinder extending along an axis from a rear end of the cylinder to a front end of the cylinder;
   a piston disposed in the cylinder, the piston dividing the cylinder into an actuation chamber at the rear end of the cylinder and a ventilation chamber at the front end of the cylinder, the actuation chamber configured to be in fluid communication with a resuscitator bag, and the ventilation chamber in fluid communication with a patient interface port configured for connection with a patient interface to direct gas into the lungs of a patient; and
   a volume adjuster coupled to the cylinder and configured to adjust a maximum displacement volume of the piston in the cylinder, the volume adjuster being adjustable between a bypass mode which allows gases from the actuation chamber to bypass the piston to enter the ventilation chamber and a volume control mode in which the piston prevents movement of gases from the actuation chamber into the ventilation chamber;
   wherein pressurized gas introduced into the actuation chamber causes the piston to travel toward the front end of the cylinder and force gas out of the ventilation chamber toward the patient interface port.

18. The ventilation control assembly of claim 17, wherein the volume control mode is between the bypass mode in which the cylinder is retracted into an adjuster body of the volume adjuster and a zero-displacement mode in which the cylinder is fully extended from the adjuster body and provides zero effective volume of the ventilation chamber.

19. The ventilation control assembly of claim 17, wherein the volume adjuster includes a piston stop surface that engages the piston and stops travel of the piston toward the rear end of the cylinder, and wherein the volume adjuster selectively shifts the piston stop surface axially forward and rearward along the cylinder.

20. The ventilation control assembly of claim 19, wherein the volume adjuster is threadedly engaged with the cylinder, wherein twisting the volume adjuster in a first direction advances the piston stop surface toward the front end of the cylinder and twisting the volume adjuster in a second direction retracts the piston stop surface toward the rear end of the cylinder.

* * * * *